US012805791B2

(12) United States Patent
Gupta et al.

(10) Patent No.: US 12,805,791 B2
(45) Date of Patent: Nov. 24, 2026

(54) ARTIFICIAL INTELLIGENCE-MACHINE LEARNING (AI-ML) BASED METHOD AND DEVICE FOR DETECTING FRACTURE

(71) Applicant: MyDigiRecords, Inc., Kansas City, MO (US)

(72) Inventors: Saroj Gupta, Overland Park, KS (US); Abhimanyu Gupta, Overland Park, KS (US)

(73) Assignee: MyDigiRecords, Inc.

( * ) Notice: Subject to any disclaimer, the term of this patent is extended or adjusted under 35 U.S.C. 154(b) by 144 days.

(21) Appl. No.: 18/827,903

(22) Filed: Sep. 9, 2024

(65) Prior Publication Data

US 2026/0069200 A1 Mar. 12, 2026

(51) Int. Cl.
*A61B 5/00* (2006.01)
*A61B 5/01* (2006.01)
*A61B 5/107* (2006.01)
*G06T 7/00* (2017.01)

(52) U.S. Cl.
CPC ............ *A61B 5/4504* (2013.01); *A61B 5/015* (2013.01); *A61B 5/1079* (2013.01); *A61B 5/4842* (2013.01); *A61B 5/6898* (2013.01); *A61B 5/7267* (2013.01); *G06T 7/0014* (2013.01); *G06T 2207/10048* (2013.01); *G06T 2207/20081* (2013.01); *G06T 2207/30008* (2013.01)

(58) Field of Classification Search
CPC ..... A61B 5/0077; A61B 5/4504; A61B 5/015; A61B 5/1079; A61B 5/7267
See application file for complete search history.

(56) References Cited

U.S. PATENT DOCUMENTS

| | | | | |
|---|---|---|---|---|
| 11,935,654 B2 | 3/2024 | Li et al. | | |
| 2023/0200762 A1* | 6/2023 | Singh | A61B 6/547 378/62 | |

FOREIGN PATENT DOCUMENTS

| | | | | |
|---|---|---|---|---|
| CN | 202128485 | * | 2/2012 | A61B 5/4504 |
| CN | 117593293 | A | 2/2024 | |
| IN | 202311036287 | | 6/2023 | |
| IN | 202441000558 | | 2/2024 | |
| WO | WO2022257314 | A1 | 2/2021 | |
| WO | WO2022139246 | A1 | 6/2022 | |

* cited by examiner

*Primary Examiner* — Robert L Nasser
(74) *Attorney, Agent, or Firm* — S.J. INTELLECTUAL PROPERTY LTD.

(57) ABSTRACT

Present disclosure describes techniques for detecting fracture. The techniques include the step of capturing a plurality of images of an affected area from different angles. The techniques further include the step of determining surface temperature of the affected area, comparing, using an AI-ML model, the captured plurality of images with baseline images or a digital twin to detect change in at least one of: size, shape, or contour of the affected area, identifying swelling in the affected area based on the detected change in the at least one of: size, shape, or contour of the affected area, correlating the swelling related data with the determined surface temperature to assess an underlying issue. The techniques further include the step of generating a severity index based on correlation between the swelling related data and determined surface temperature.

11 Claims, 8 Drawing Sheets

ARTIFICIAL INTELLIGENCE-MACHINE LEARNING (AI-ML) BASED METHOD AND DEVICE FOR DETECTING FRACTURE

BACKGROUND OF THE INVENTION

Technical Field

The present disclosure relates to artificial intelligence (AI) and machine learning based application. Particularly, the based present disclosure relates to AI based method and AI based system for detecting fracture.

Description of the Related Art

When a bone gets fractured, there are many devices such as X-Ray and MRI to detect such fracture and take appropriate measures. The costs of medical imaging machines can vary significantly based on the type of machine, its features, and the location where it is purchased and operated. The costs associated with common imaging machines includes their purchase prices, yearly maintenance, and operating costs.

The costs for training radiologists and technicians to operate the equipment add to overall cost. These medical imaging machines comes with space requirements, utility costs, and infrastructure modifications which are essentially required for housing and operating the machines. These costs can vary widely based on the specific model, location, and additional features or services included. In addition, some of these machines may require more frequent updates or repairs, which can affect the overall cost.

In rural areas, it is not feasible to bring such large investments. The medical costs associated with delayed detection and treatment of fractures can increase significantly, especially when considering additional complications and the need for extended care. For example, a fracture that isn't detected timely and treated promptly can lead to malunion (improper alignment) or nonunion (failure to heal), which may require corrective surgery. Open fractures or delayed treatment of closed fractures can lead to infections, requiring antibiotics, and sometimes surgical intervention.

Delayed treatment can lengthen the recovery period, increasing the need for physical therapy. Inadequately treated fractures can lead to chronic pain, requiring long-term pain management. Further, delayed treatment can result in longer periods off work, affecting income and productivity.

Currently, several exciting non-invasive methods are being explored to detect bone fractures, eliminating the need for traditional X-rays and their associated drawbacks like radiation exposure. Such as MRI, Ultrasound, and Acoustic Emission Monitoring that listen for sound waves emitted by bone as it cracks or fractures, Biomarkers that investigates blood or urine markers that signal bone tissue breakdown associated with fractures, Electrical Impedance Spectroscopy (EIS) that measures the electrical conductivity of bone, which changes due to fractures. However, the issue with these techniques is that they all require hardware and are expensive to build.

For the aforementioned reasons, there exist a need in the art to provide a technique which overcomes the above-mentioned problems and efficiently and effectively detect fractures using existing capabilities of smart phones that are widely available.

SUMMARY OF THE INVENTION

In one non-limiting embodiment of the present disclosure, an artificial intelligence (AI) based method for detecting fracture is disclosed. The method comprises capturing a plurality of images of an affected area from different angles and determining surface temperature of the affected area. The surface temperature indicates potential inflammation or infection. The method further comprises comparing, using an AI-ML model, the captured plurality of images with baseline images or a digital twin to detect change in at least one of: size, shape, or contour of the affected area and identifying swelling in the affected area based on the detected change in the at least one of: size, shape, or contour of the affected area. The method finally includes correlating the swelling related data with the determined surface temperature to assess an underlying issue and generating a severity index based on correlation between the swelling related data and determined surface temperature.

In another non-limiting embodiment of the present disclosure, the method further comprises providing one or more recommendations based on the severity index. The one or more recommendations at least include seeking medical attention, applying first aid, or monitoring existing condition.

In yet another non-limiting embodiment of the present disclosure, the determining the surface temperature of the affected area comprises measuring surface temperature of the affected area at least based on temperature captured using thermal imaging camera.

In yet another non-limiting embodiment of the present disclosure, the determining the surface temperature of the affected area comprises estimating, using the AI-ML model, the surface temperature of the affected area based on visual cues of the affected present in the plurality of images.

In yet another non-limiting embodiment of the present disclosure, the method further comprises receiving a plurality of sample images of each human body part and training the AI-ML model with plurality of sample image of each body part for classifying each body part.

In yet another non-limiting embodiment of the present disclosure, the method further comprises providing the AI-ML model with a plurality of baseline images. The plurality of baseline images is captured before injury.

In yet another non-limiting embodiment of the present disclosure, the method further comprises receiving a plurality of images of a person before the injury and generating, using an extended reality model, a digital twin of a person beforehand for comparison.

In yet another non-limiting embodiment of the present disclosure, the method further comprises providing a plurality of sample injury images and training the AI-ML model for feature detection such as detection of size, shape, and contour of the affected area in the plurality of sample injury images and for classification of different signs of swelling in the sample injury images.

In yet another non-limiting embodiment of the present disclosure, the method further comprises providing a plurality of sample injury images and respective temperature and training the AI-ML model for estimation of temperature based on visual cues of plurality of sample injury images, wherein the visual cues at least include redness or swelling.

In yet another non-limiting embodiment of the present disclosure, an artificial intelligence (AI) based device for detecting fracture is disclosed. The AI based device comprises a memory for storing a plurality of instructions, at least one image sensor, at least one processor coupled to the at least one image sensor and the memory. The at least one processor is configured to capture a plurality of images of an affected area from different angles and determine surface temperature of the affected area. The surface temperature indicates potential inflammation or infection. The at least one processor is configured to compare, using an AI-ML model, the captured plurality of images with baseline images or a digital twin to detect change in at least one of: size, shape, or contour of the affected area and identify swelling in the affected area based on the detected change in the at least one of: size, shape, or contour of the affected area. The at least one processor is then configured to correlate the swelling related data with the determined surface temperature to assess an underlying issue and generate a severity index based on correlation between the swelling related data and determined surface temperature.

In yet another non-limiting embodiment of the present disclosure, the at least one processor is configured to provide one or more recommendations based on the severity index. The one or more recommendations at least include seeking medical attention, applying first aid, or monitoring existing condition.

In yet another non-limiting embodiment of the present disclosure, to determine the surface temperature of the affected area, the at least one processor is configured to measure surface temperature of the affected area at least based on temperature captured using thermal imaging camera.

In yet another non-limiting embodiment of the present disclosure, to determine the surface temperature of the affected area, the at least one processor is configured to estimate, using the AI-ML model, the surface temperature of the affected area based on visual cues of the affected present in the plurality of images.

In yet another non-limiting embodiment of the present disclosure, the at least one processor is configured to receive a plurality of sample images of each human body part and train the AI-ML model with plurality of sample image of each body part for classifying each body part.

In yet another non-limiting embodiment of the present disclosure, the at least one processor is configured to provide the AI-ML model with a plurality of baseline images. The plurality of baseline images is captured before injury.

In yet another non-limiting embodiment of the present disclosure, the at least one processor is configured to receive a plurality of images of a person before the injury and generate, using, an extended reality model, a digital twin of a person beforehand for comparison.

In yet another non-limiting embodiment of the present disclosure, the at least one processor is configured to provide a plurality of sample injury images and train the AI-ML model for feature detection such as detection of size, shape, and contour of the affected area in the plurality of sample injury images and for classification of different signs of swelling in the sample injury images.

In yet another non-limiting embodiment of the present disclosure, the at least one processor is configured to provide a plurality of sample injury images and respective temperature and train the AI-ML model for estimation of temperature based on visual cues of plurality of sample injury images, wherein the visual cues at least include redness or swelling.

In yet another non-limiting embodiment of the present disclosure, a non-transitory computer-readable medium is disclosed. The non-transitory computer-readable medium comprises computer-readable instructions that when executed by a processor causes the processor to perform operations of capturing a plurality of images of an affected area from different angles, determining surface temperature of the affected area, comparing, using an AI-ML model, the captured plurality of images with baseline images or a digital twin to detect change in at least one of: size, shape, or contour of the affected area, identifying swelling in the affected area based on the detected change in the at least one of: size, shape, or contour of the affected area, correlating the swelling related data with the determined surface temperature to assess an underlying issue, and generating a severity index based on correlation between the swelling related data and determined surface temperature.

The foregoing summary is illustrative only and is not intended to be in any way limiting. In addition to the illustrative embodiments, and features described above, further embodiments, and features will become apparent by reference to the drawings and the following detailed description.

BRIEF DESCRIPTION OF DRAWINGS

The accompanying drawings, which are incorporated in and constitute a part of this disclosure, illustrate exemplary embodiments and, together with the description, serve to explain the disclosed principles. Some embodiments of system and/or methods in accordance with embodiments of the present subject matter are now described, by way of example only, and with reference to the accompanying Figures, in which.

Figure 1:
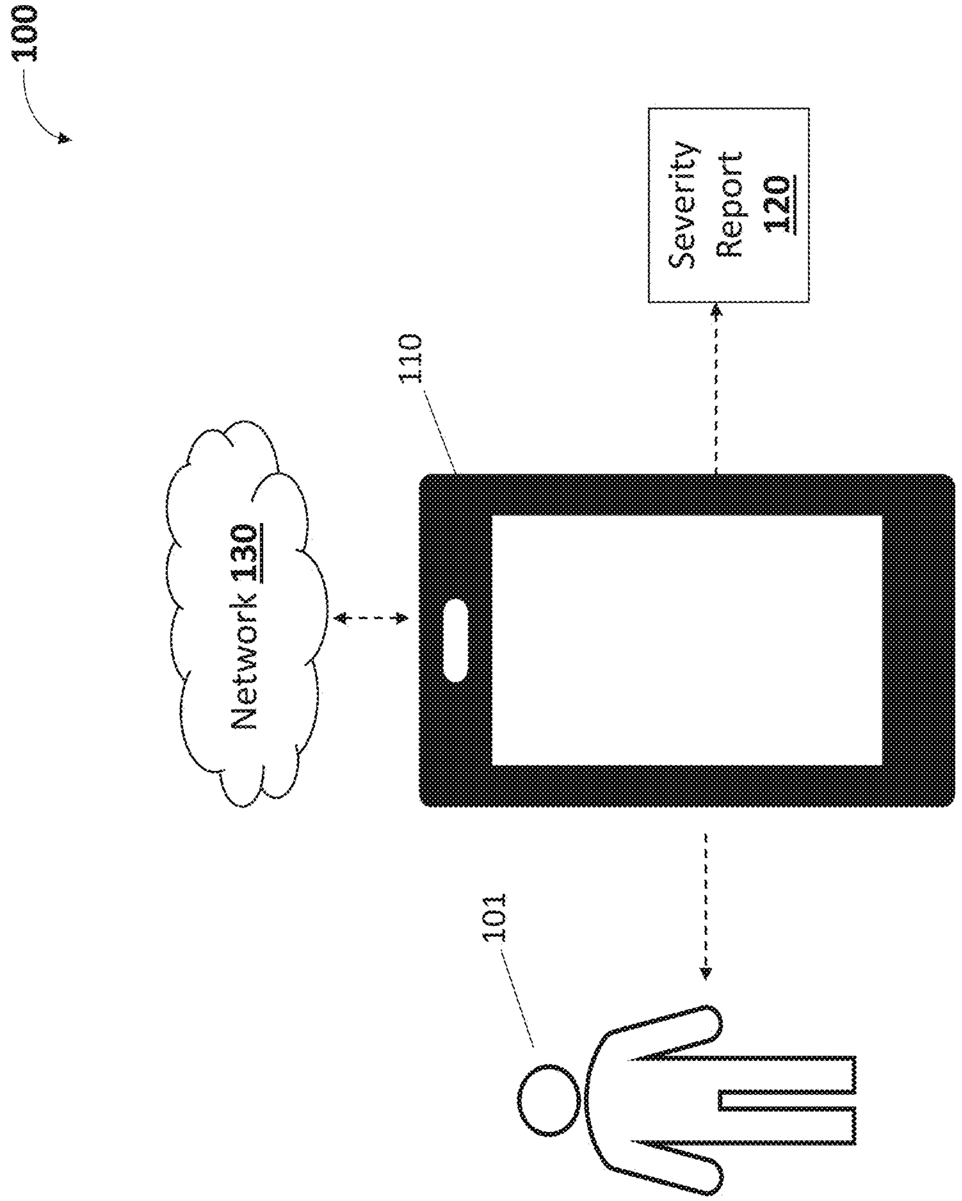
FIG. 1 shows an exemplary environment for fracture detection, in accordance with some embodiments of the present disclosure.

It should be appreciated by those skilled in the art that any block diagrams herein represent conceptual views of the illustrative systems embodying the principles of the present subject matter. Similarly, it will be appreciated that any flowcharts, flow diagrams, state transition diagrams, pseudo code, and the like represent various processes which may be substantially represented in computer readable medium and executed by a computer or processor, whether or not such computer or processor is explicitly shown.

DETAILED DESCRIPTION OF THE EMBODIMENTS

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiments thereof have been shown by way of example in the drawings and will be described in detail below. It should be understood, however, that these embodiments are not intended to limit the disclosure to the particular form disclosed, but on the contrary, the disclosure is to cover all modifications, equivalents, and alternatives falling within the spirit and the scope of the disclosure.

The terms "comprise(s)", "comprising", "include(s)", or any other variations thereof, are intended to cover a non-exclusive inclusion, such that a setup, device, apparatus, system, or method that comprises a list of components or steps does not include only those components or steps but may include other components or steps not expressly listed or inherent to such setup or device or apparatus or system or method. In other words, one or more elements in a device or system or apparatus proceeded by "comprises . . . a" does not, without more constraints, preclude the existence of other elements or additional elements in the system.

The expressions like "at least one" and "one or more" may be used interchangeably or in combination throughout the description.

In the following detailed description of the embodiments of the disclosure, reference is made to the accompanying drawings that form a part hereof, and in which are shown by way of illustration of specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense. In the following description, well known functions or constructions are not described in detail since they would obscure the description with unnecessary detail.

FIG. 1 shows an exemplary environment for fracture detection, in accordance with some embodiments of the present disclosure.

The environment 100 comprises a patient or a subject 101, a user device 110, and a network 130 in communication with each other. The user devices may include, for example, a mobile phone, a laptop, a tablet, a desktop computer, and/or the like. However, the user device is not limited to above examples, and may include any other device known to a person skilled in the art.

The network 130 may include, for example, the Internet, a private network, public network or other configuration that operates using any one or more known communication protocols such as, for example, transmission control protocol/Internet protocol (TCP/IP). Other examples of the communication protocols include Bluetooth®, BLE®, Wi-Fi, UWB, and cellular technologies such as Time Division Multiple Access (TDMA), Code Division Multiple Access (CDMA), High Speed Packet Access (HSPDA), Long-Term Evolution (LTE), Global System for Mobile Communications (GSM), and Fifth Generation (5G), to name a few.

The user device 110 may include a plurality of sensors comprising an image sensor. The user device 110 may be configured to take a plurality of images of an affected/injured area of the subject or the patient 101. The plurality of images of the affected/injured area may be processed to detect fracture in the affected/injured area. The user device 110 may be configured to generate a severity report of the injury and the severity report may include one or more recommendations such as seeking medical attention, applying first aid, or monitoring existing condition. Thus, the user device 101 prevents delayed detection and treatment of fractures.

Figure 2:
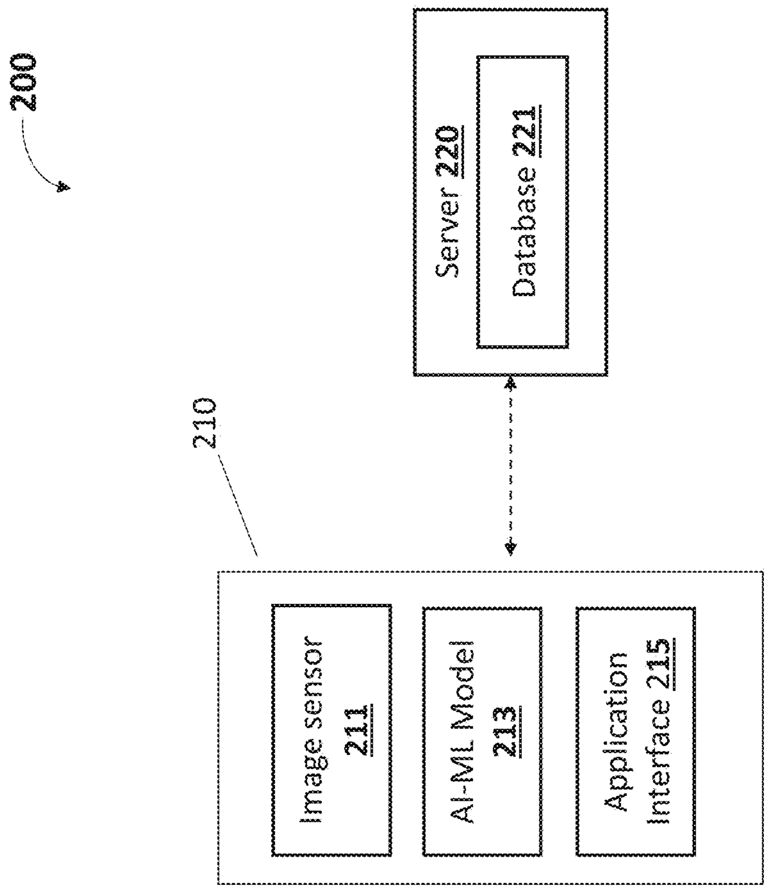
FIG. 2 illustrates an exemplary interaction between a user device and a server, in accordance with some embodiments of the present disclosure.

FIG. 2 illustrates an exemplary interaction 200 between a user device and a server, in accordance with some embodiments of the present disclosure.

In an aspect of the present disclosure, the user device 210 may comprise an image sensor 211, an AI-ML model 213, and an application interface 215 in communication with each other. The image sensor 211 and the AI-ML model 213 may be configured to detect fractures based on images of the affected/injured area.

In one non-limiting aspect, the user device 210 may comprise or may be coupled to thermal imaging sensor (not shown) that may be configured to measure surface temperature of the affected area and detect symptoms of fracture based on the measured surface temperature of the affected area. The thermal imaging sensor may aid in confirming the fracture after the image based detection. The user device 210 may be coupled to the server 220 for storing data associated with the user/patient.

In an aspect of the present disclosure, the database 221 may be configured to store baseline images of different body parts of the user/patient before the injury. Further, the database 221 may also be configured to store medical history including past injuries of the patient or the user for later reference. In one non-limiting aspect, the medical history may be retrieved from the server 220 to determine the severity level or severity score of the injury.

In one non-limiting aspect, the AI-ML model 213 may be located at the server 220 and the server 220 may be configured to receive plurality of images of the affected area and to determine the fracture using the AI-ML model 213 located at the server 220.

Thus, the user device 210 effectively detects fractures using existing capabilities of smart phones that are widely available and prevents delayed detection and treatment of fractures.

Figure 3A:
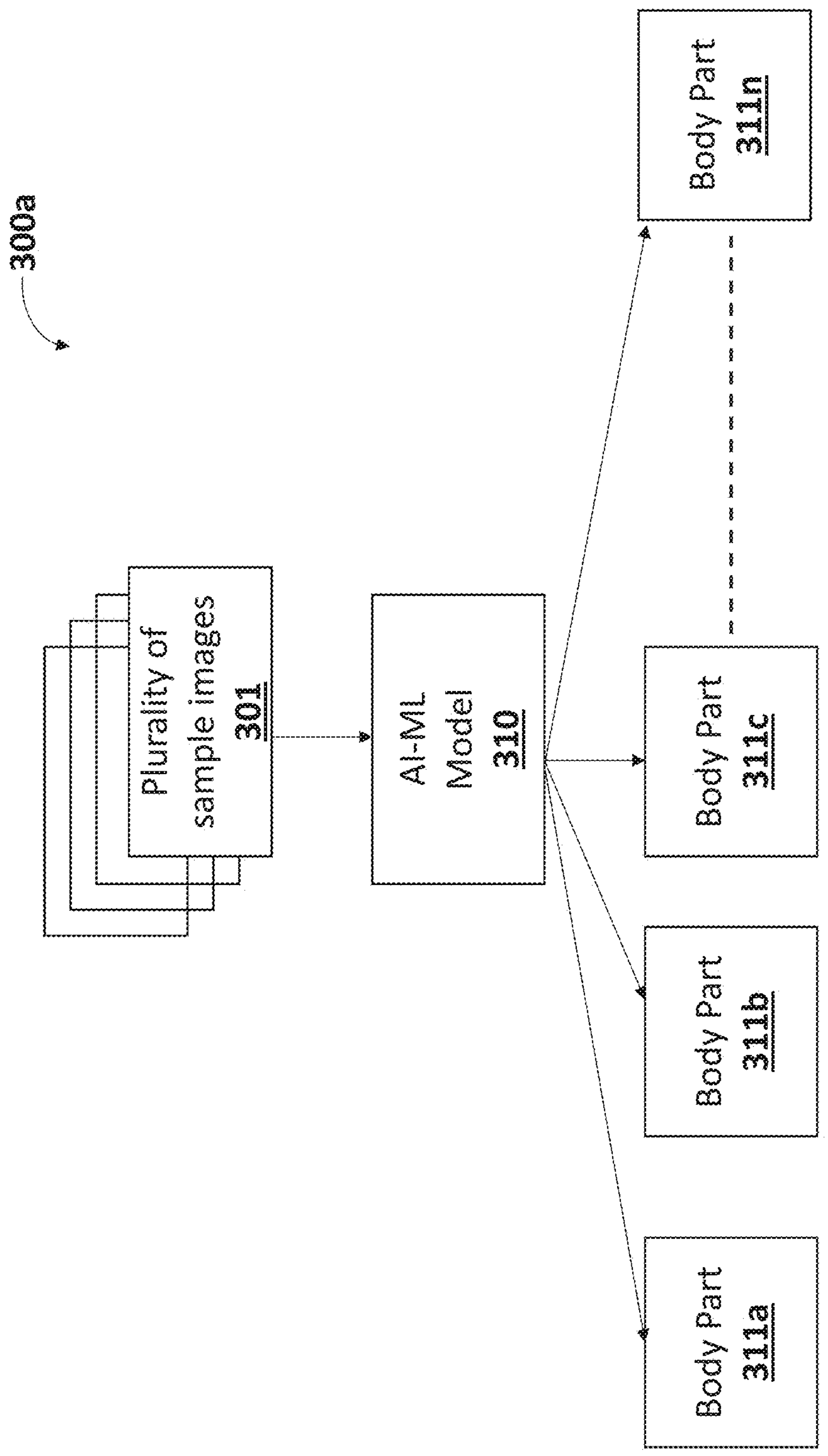
FIG. 3*a* illustrates an exemplary block diagram for training an AI-ML model for body part identification of a user, in accordance with some embodiments of the present disclosure.

FIG. 3*a* illustrates an exemplary block diagram 300*a* for training an AI-ML model for body part identification of a user, in accordance with some embodiments of the present disclosure.

In an aspect of the present disclosure, the AI-ML model 310 may be trained with a plurality of sample images 301. The AI-ML model 310 may be configured to receive the plurality of sample images 301 and indication of respective body part 311*a*, 311*b*, 311*c*, . . . 311*n*, associated with each sample image. The AI-ML model 310 may be configured to classify the image with the respective body part 311*a*, 311*b*, 311*c*, . . . 311*n*.

The AI-ML model 310 may be configured to receive real time images of an affected area of the patient and to identify the body part corresponding to the affected area of the patient. This identification of the body part may be further utilized by the AI-ML model 310 for feature detection in the affected area of the patient. The identification of the body part helps in identifying the swelling in the affected area by providing correct set of reference images for comparison.

Figure 3B:
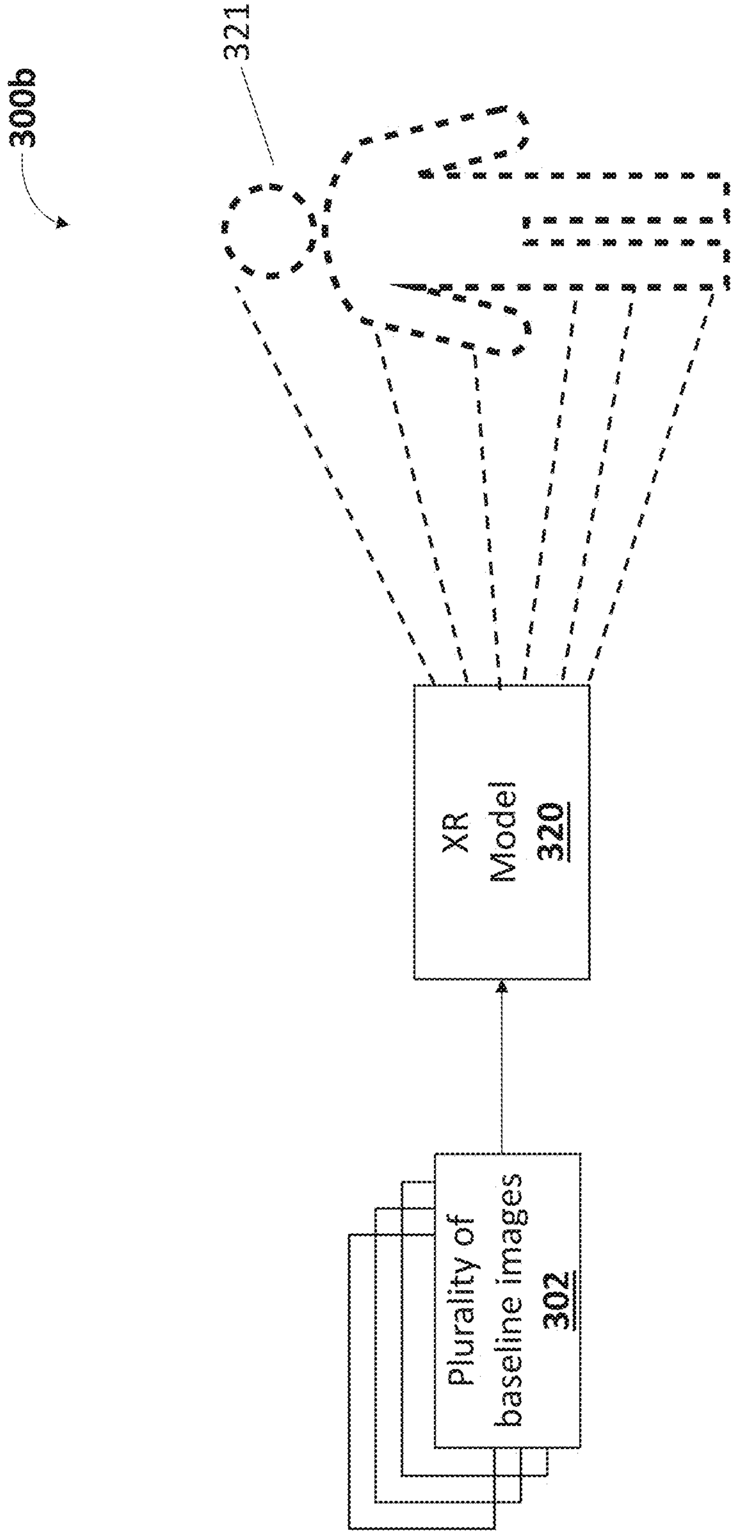
FIG. 3*b* illustrates an exemplary block diagram for generation of digital twin of the user, in accordance with some embodiments of the present disclosure.

FIG. 3*b* illustrates an exemplary block diagram 300*b* for generation of digital twin of the user, in accordance with some embodiments of the present disclosure.

In an aspect of the present disclosure, the user may capture a plurality of baseline images 302 of the user/patient. The baseline images 302 are the images captured before the injury to the patient. The captured images may be then provided to an extended reality model 320 and the extended reality model 320 may be configured to generate a digital twin 321 of the user/patient beforehand for comparison.

The generated digital twin 321 of the user/patient may be compared with the images of the injury to detect change in at least one of: size, shape, or contour of the affected area and identify swelling based on the detected change. In one non-limiting aspect, the generation of the digital twin 321 by the extended reality model 320 is optional and the images of the injury may be directly compared with the plurality of baseline images 302 to detect change in at least one of: size, shape, or contour of the affected area, as discussed in below aspects in further detail.

Figure 3C:
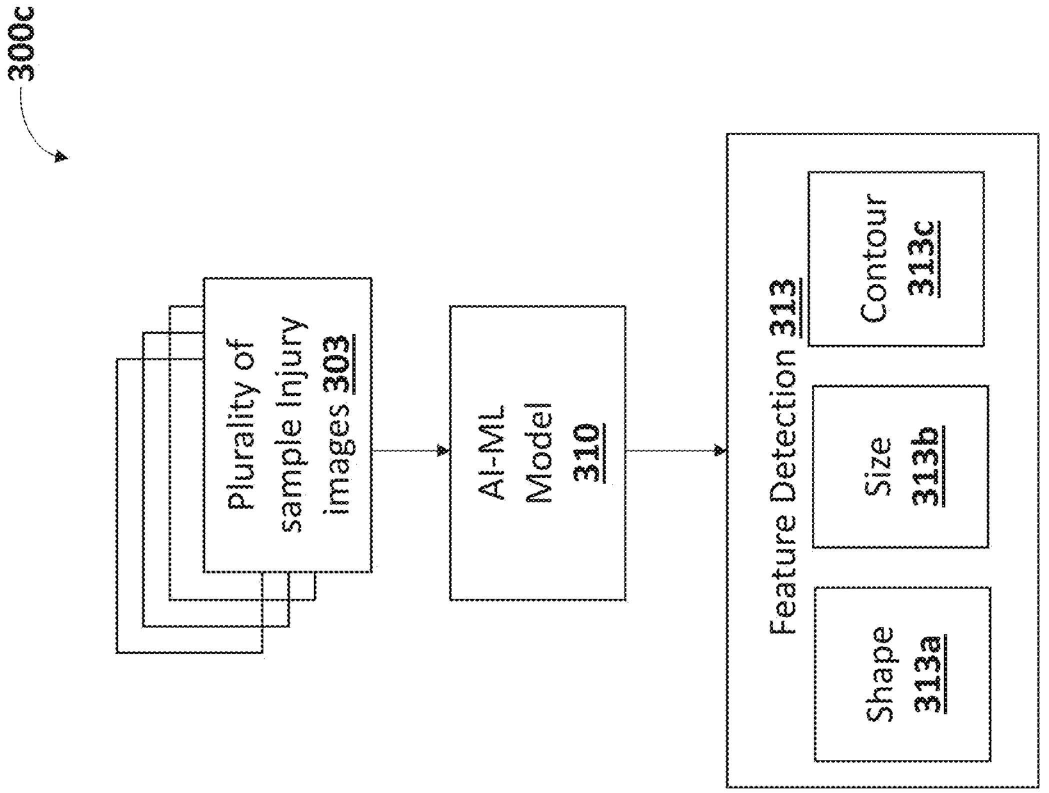
FIG. 3*c* shows a block diagram of training an AI-ML model for swelling related feature detection, in accordance with some embodiments of the present disclosure.

FIG. 3*c* shows a block diagram of training an AI-ML model for swelling related feature detection, in accordance with some embodiments of the present disclosure.

In an aspect of the present disclosure, an injured body part is determined based on training of AI-ML model 310 discussed in reference with FIG. 3*a*. Then, the AI-ML model 310 is provided with a plurality of sample injury images 303 and the AI-ML model 310 is trained for feature detection such as detection of size, shape, and contour of affected area present in the plurality of sample injury images and for classification of different signs of swelling in the sample injury images.

In one non-limiting aspect, the trained AI-ML model 310 may be a deep neural network or convolution neural network model. Further, the feature detection technique may include one of: Harris Corner Detection, Shi-Tomasi Corner Detection, Canny Edge Detection, Blob Detection, Scale-Invariant Feature Transform (SIFT), etc. However, the feature detection technique is not limited to above example and any other technique known to a person skilled in the art is well within the scope of present disclosure.

Once the AI-ML model 310 is trained, the AI-ML model 310 may be used to detect change in at least one of: size, shape, or contour of affected area of the patient and identify swelling in the affected area based on the detected change in the at least one of: size, shape, or contour of the affected area.

This facilitates effective detection of fractures using existing capabilities of smart phones that are widely available and prevention of delayed detection and treatment of fractures.

Figure 3D:
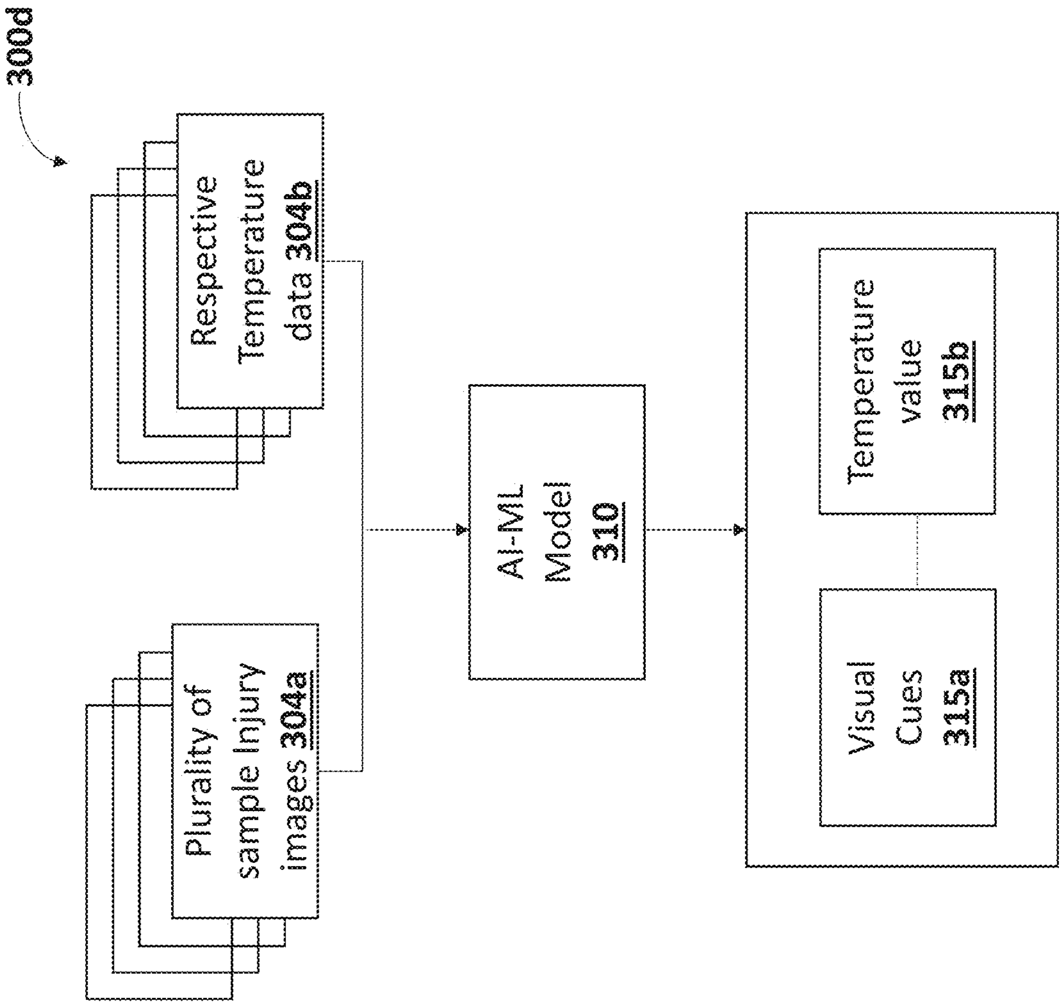
FIG. 3*d* shows a block diagram of training an AI-ML model for estimating temperature based on visual cues, in accordance with some embodiments of the present disclosure.

FIG. 3*d* shows a block diagram of training an AI-ML model 310 for estimating temperature based on visual cues, in accordance with some embodiments of the present disclosure.

In an aspect of the present disclosure, the AI-ML model 310 may be provided a plurality of sample injury images 304*a* and respective temperature data 304*b*. Then, the AI-ML model 310 is trained for estimation of temperature based on visual cues of plurality of sample injury images 304*a*. The visual cues may at least include redness or swelling. Thus, the AI-ML model 310 may classify each visual cue 315*a* with respective temperature value 315*b*.

When the injury has occurred, a plurality of images from different angles are captured and the AI-ML model 310 may be used to estimate the surface temperature of the affected area based on visual cues of the affected present in the plurality of images. The thermal data or the surface temperature may be processed to identify areas of increased temperature, indicating potential inflammation or infection.

Figure 4:
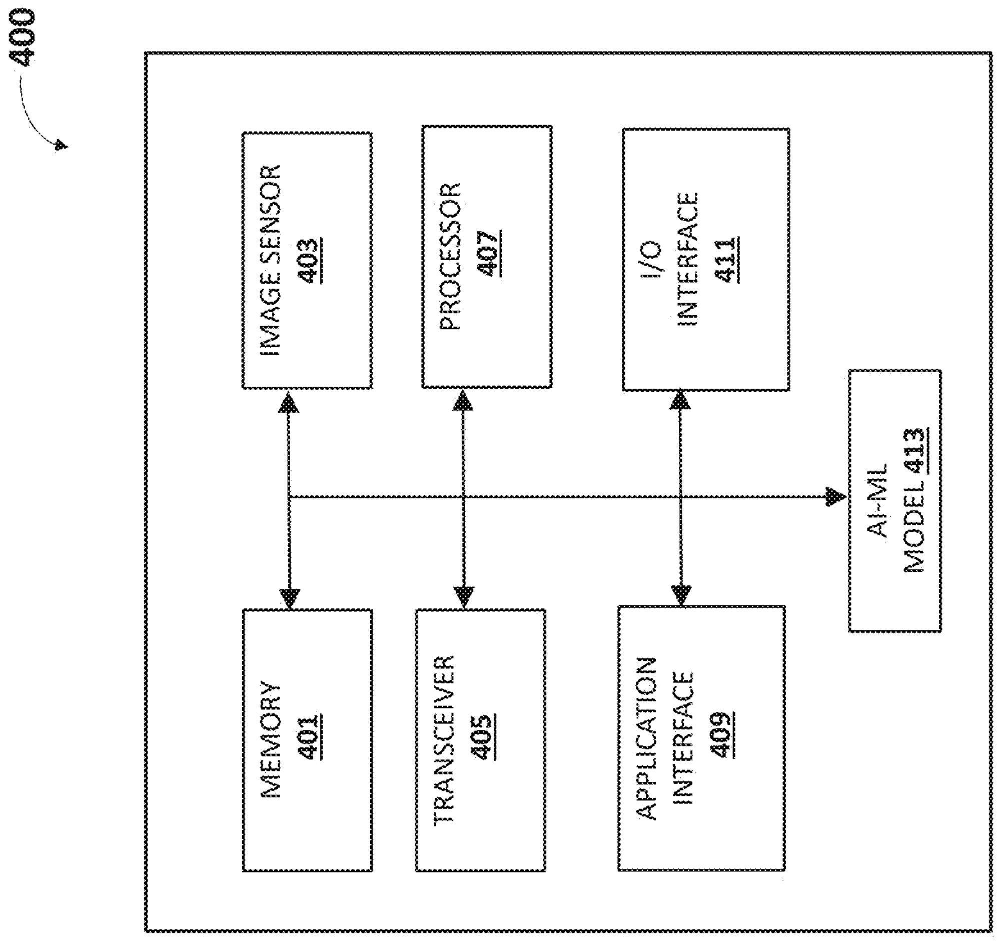
FIG. 4 shows a block diagram of an artificial intelligence (AI) based device for detecting fracture, in accordance with some embodiments of the present disclosure.

FIG. 4 shows a block diagram of an artificial intelligence (AI) based device 400 for detecting fracture, in accordance with some embodiments of the present disclosure.

The AI based device 400 may be a user device such as, but not limited to, mobile phone, laptop, computer, etc. The AI based device 400 may comprise a memory 401, image sensor(s) 403, a transceiver 405, processor 407, application interface 409, input output (I/O) interface 411, and AI-ML model 413 in communication with each other. In one non-limiting aspect, the AI based device 400 may also comprise a thermal imaging sensor (not shown) and the thermal imaging sensor may be configured to measure surface temperature of an affected area for determining or confirming the fracture.

The memory 401 may be configured to store a plurality of instructions to be executed by the processor 407 for performing various functionalities of the user device. The transceiver 405 may be configured to receive and transmit data from/to different devices/sensors. The application interface 409 may be user interface required by the user of the AI based device 400 for accessing the functionality of detecting fracture.

The processor 407 may be configured to capture, using the image sensor 403, a plurality of images of an affected area from different angles. The application interface 409 may be configured to guide the user to align the device 400 at different angles and capture the plurality of images of the affected area from different angles.

The processor 407 may be then configured to determine surface temperature of the affected area. The surface temperature may be used identify a potential inflammation or an infection. In an aspect of the present disclosure, to determine the surface temperature of the affected area the processor 407 may be configured to measure surface temperature of the affected area at least based on temperature captured using thermal imaging camera.

In another aspect of the present disclosure, to determine the surface temperature of the affected area the processor 407 may be configured to estimate, using the AI-ML model 413, the surface temperature of the affected area based on visual cues of the affected present in the plurality of images. The AI-ML model 413 may be trained to determine surface temperature of the affected area, as discussed in detail with reference to FIG. 3*d*.

The processor 407 may be then configured to compare the captured plurality of images with baseline images or a digital twin to detect change in at least one of: size, shape, or contour of the affected area. The comparison may be carried out using the AI-ML model 413. The AI-ML model 413 may be trained to detect change in at least one of: size, shape, or contour of the affected area, using the feature detection technique, as discussed in above aspects.

The processor 407 may be then configured to identify swelling in the affected area based on the detected change in the at least one of: size, shape, or contour of the affected area. The detected change may be observed based on the feature detection technique as discussed in above aspect.

The processor 407 may be then configured to correlate the swelling related data with the determined surface temperature to assess an underlying issue. The underlying issue may comprise different type of medical conditions associated with the fractures. The processor 407 may be configured to generate a severity index based on correlation between the swelling related data and determined surface temperature.

The severity index may indicate the seriousness of the injury and type of medical attention needed for the patient.

The processor 407 may be further configured to provide one or more recommendations based on the severity index. The one or more recommendations at least include seeking medical attention, applying first aid, or monitoring existing condition. In one non-limiting aspect of the present disclosure, the AI-ML model 413 may be trained with one or more recommendations associated with respective severity index. Further, the user is provided with appropriate recommendations based on the severity of the injury.

Thus, the AI based device 400 facilitates identification potential issues like fractures, infections, or severe inflammation and guidance to users to seek medical care promptly, potentially preventing complications. Further, the AI based device 400 is useful in rural or underserved areas where access to medical facilities is limited and reduces the need for immediate travel to healthcare facilities for initial assessments. In addition, the AI based device 400 provides users with information to make informed decisions about their health and treatment options and helps in remote consultations by providing detailed preliminary assessments.

Figure 5:
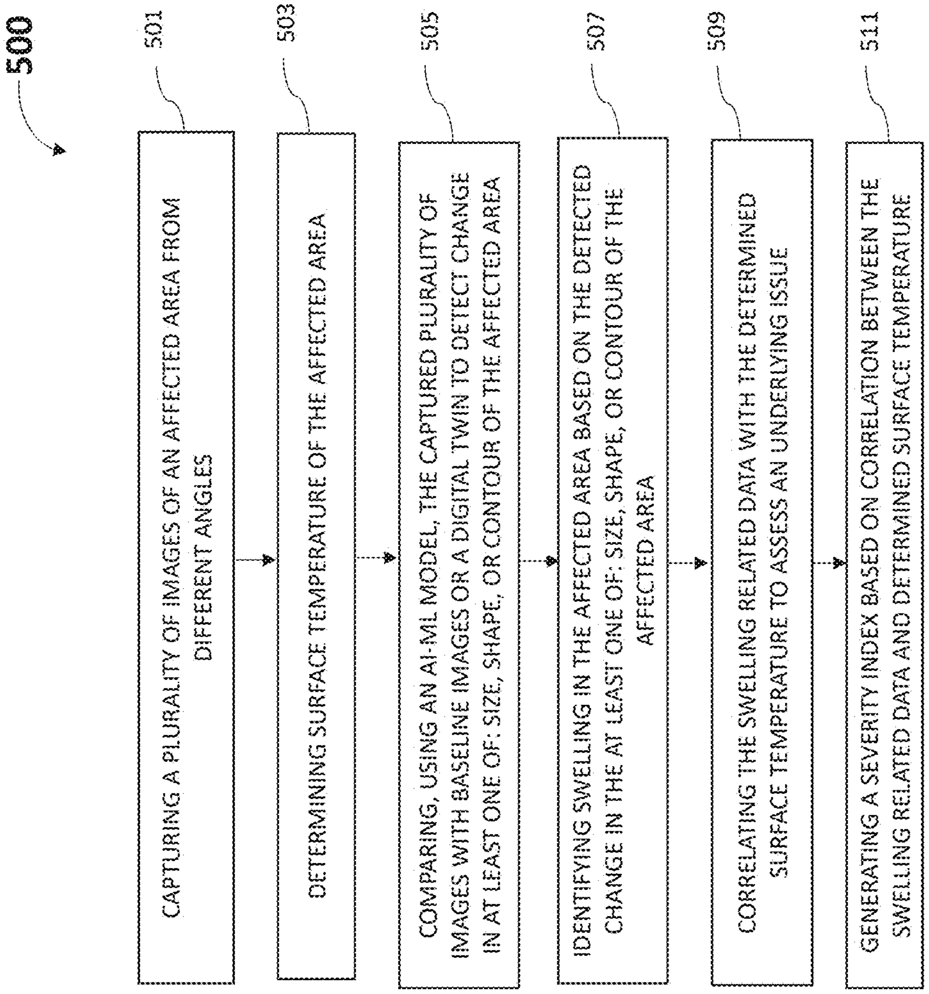
FIG. 5 depicts a flowchart illustrating an exemplary artificial intelligence (AI) based method for detecting fracture, in accordance with some embodiments of the present disclosure.

FIG. 5 depicts a flowchart illustrating an exemplary artificial intelligence (AI) based method for detecting fracture, in accordance with some embodiments of the present disclosure.

At step 501, the method 500 discloses capturing, using the image sensor 403, a plurality of images of an affected area from different angles. In an aspect, the application interface 409 may guide the user to align the device at different angles and capture the plurality of images of the affected area from different angles.

At step 503, the method 500 discloses determining surface temperature of the affected area. The surface temperature may be used identify a potential inflammation or an infection. In an aspect of the present disclosure, for determining the surface temperature of the affected area the method 500 discloses measuring surface temperature of the affected area at least based on temperature captured using thermal imaging camera.

In another aspect of the present disclosure, for determining the surface temperature of the affected area the method 500 discloses estimating, using the AI-ML model 413, the surface temperature of the affected area based on visual cues of the affected present in the plurality of images. The AI-ML model 413 may be trained to determine surface temperature of the affected area, as discussed in detail with reference to FIG. 3*d*.

At step 505, the method 500 discloses comparing the captured plurality of images with baseline images or a digital twin to detect change in at least one of: size, shape, or contour of the affected area. The comparison may be carried out using the AI-ML model 413. The AI-ML model 413 may be trained to detect change in at least one of: size, shape, or contour of the affected area, using the feature detection technique, as discussed in above aspects.

At step 507, the method 500 discloses identifying swelling in the affected area based on the detected change in the at least one of: size, shape, or contour of the affected area. The detected change may be observed based on the feature detection technique as discussed in above aspect.

At step 509, the method 500 discloses correlating the swelling related data with the determined surface temperature to assess an underlying issue. The underlying issue may comprise different type of medical conditions associated with the fractures.

At step 511, the method 500 discloses generating a severity index based on correlation between the swelling related data and determined surface temperature. The severity index may indicate the seriousness of the injury and type of medical attention needed for the patient.

The method 500 further discloses providing one or more recommendations based on the severity index. The one or more recommendations at least include seeking medical attention, applying first aid, or monitoring existing condition. In one non-limiting aspect of the present disclosure, the AI-ML model 413 may be trained with one or more recommendations associated with respective severity index. Further, the user is provided with appropriate recommendations based on the severity of the injury.

Thus, the AI based method 500 facilitates identification potential issues like fractures, infections, or severe inflammation and guidance to users to seek medical care promptly, potentially preventing complications. Further, the AI based method 500 is useful in rural or underserved areas where access to medical facilities is limited and reduces the need for immediate travel to healthcare facilities for initial assessments. In addition, the AI based method 500 provides users with information to make informed decisions about their health and treatment options and helps in remote consultations by providing detailed preliminary assessments.

In another non-limiting embodiment of the present disclosure, the steps of method 500 may be performed in an order different from the order described above.

It is to be understood that not necessarily all objectives or advantages may be achieved in accordance with any particular embodiment described herein. Thus, for example, those skilled in the art will appreciate that certain embodiments may be configured to operate in a manner that achieves or optimizes one advantage or group of advantages as taught herein without necessarily achieving other objects or advantages as may be taught or suggested herein.

In a non-limiting embodiment of the present disclosure, one or more non-transitory computer-readable media may be utilized for implementing the embodiments consistent with the present disclosure. A computer-readable media refers to any type of physical memory (such as the memory) on which information or data readable by a processor may be stored. Thus, a computer-readable media may store one or more instructions for execution by the at least one processor, including instructions for causing the at least one processor to perform steps or stages consistent with the embodiments described herein. The term "computer-readable media" should be understood to include tangible items and exclude carrier waves and transient signals. By way of example, and not limitation, such computer-readable media can comprise Random Access Memory (RAM), Read-Only Memory (ROM), volatile memory, nonvolatile memory, hard drives, Compact Disc (CD) ROMs, Digital Video Disc (DVDs), flash drives, disks, and any other known physical storage media.

Thus, certain aspects may comprise a computer program product for performing the operations presented herein. For example, such a computer program product may comprise a computer readable media having instructions stored (and/or encoded) thereon, the instructions being executable by one or more processors to perform the operations described herein. For certain aspects, the computer program product may include packaging material.

The terms "an embodiment", "embodiment", "embodiments", "the embodiment", "the embodiments", "one or more embodiments", "some embodiments", and "one embodiment", "other embodiment", "yet another embodiment", "non-limiting embodiment" mean "one or more (but not all) embodiments of the disclosure(s)" unless expressly specified otherwise.

The various exemplary logical blocks and modules described in connection with the embodiments disclosed herein can be implemented or executed by a machine such as a processor. The processor may be a microprocessor, but alternatively, the processor may be a controller, a microcontroller, or a state machine, or a combination thereof. The processor can include an electrical circuit configured to process computer executable instructions. In another embodiment, the processor includes an application specific integrated circuit (ASIC), a field programmable gate array (FPGA), or other programmable device that performs logical operations without processing computer executable instructions. The processor can also be implemented as a combination of computing devices, e.g., a combination of a digital signal processor (DSP) and a microprocessor, a plurality of microprocessors, one or more microprocessors in conjunction with a DSP core, or any other such configuration. Although described herein primarily with respect to digital technology, the processor may also include primarily analog components. For example, some or all of the signal processing algorithms described herein may be implemented by analog circuitry or mixed analog and digital circuitry. A computing environment may include any type of computer system, including, but not limited to, a computer system that is based on a microprocessor, mainframe computer, a digital signal processor, a portable computing device, a device controller, or a computing engine within the device.

The terms "including", "comprising", "having" and variations thereof mean "including but not limited to", unless expressly specified otherwise.

The enumerated listing of items does not imply that any or all of the items are mutually exclusive, unless expressly specified otherwise.

A description of an embodiment with several components in communication with each other does not imply that all such components are required. On the contrary, a variety of optional components are described to illustrate the wide variety of possible embodiments of the disclosed methods and systems.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based here on. Accordingly, the embodiments of the present disclosure are intended to be illustrative, but not limiting, of the scope of the disclosure, which is set forth in the appended claims.

What is claimed is:

1. An artificial intelligence (AI) based method for detecting fracture, the method comprising:

capturing, using an image sensor of a smart phone device, a plurality of images of an affected area from different angles, wherein an application interface of the smart phone device guides a user to align the smart phone device at the different angles;

determining surface temperature of the affected area, wherein the surface temperature indicates potential inflammation or infection, and wherein the determining comprises at least one of:

measuring the surface temperature of the affected area at least based on a temperature captured using a thermal imaging camera, or estimating, using an AI-ML model, the surface temperature of the affected area based on visual cues of the affected area present in the plurality of images, the visual cues at least including redness or swelling, wherein the AI-ML model is trained with a plurality of sample injury images and respective temperature data to classify each visual cue with a respective temperature value;

comparing, using the AI-ML model, the captured plurality of images with baseline images or a digital twin to detect change in at least one of: size, shape, or contour of the affected area, wherein the AI-ML model is trained, using a plurality of sample injury images, to detect the change in the at least one of: size, shape, or contour of the affected area and to classify signs of swelling in the sample injury images, and wherein the AI-ML model is trained using at least one of Harris Corner Detection, Shi-Tomasi Corner Detection, Canny Edge Detection, Blob Detection, or Scale-Invariant Feature Transform (SIFT);

identifying swelling related data indicative of the swelling in the affected area based on the detected change in the at least one of: size, shape, or contour of the affected area;

correlating the swelling related data with the determined surface temperature to assess an underlying issue;

generating a severity index based on the correlation between the swelling related data and the determined surface temperature; and displaying, via a user interface of the smart phone device, one or more recommendations along with the severity index to the user.

2. The AI based method of claim 1, wherein the one or more recommendations are based on the severity index and at least include seeking medical attention, applying first aid, or monitoring existing condition.

3. The AI based method of claim 1, further comprising:

receiving a plurality of sample images of each human body part; and training the AI-ML model with the plurality of sample images of each body part for classifying each body part.

4. The AI based method of claim 1, further comprising:

providing the AI-ML model with the baseline images, wherein the baseline images are captured before injury.

5. The AI based method of claim 1, further comprising:

receiving a plurality of images of a person before an injury; and generating, using an extended reality model, the digital twin of the person beforehand for comparison.

6. An artificial intelligence (AI) based device for detecting fracture, the AI based device comprising:

a memory;

at least one image sensor;

an application interface;

at least one processor coupled to the at least one image sensor and the memory, wherein the AI based device is a smart phone device, wherein the at least one processor is configured to:

capture, using the at least one image sensor, a plurality of images of an affected area from different angles, wherein the application interface guides a user to align the smart phone device at the different angles;

determine surface temperature of the affected area, wherein the surface temperature indicates potential inflammation or infection, and wherein to determine the surface temperature the at least one processor is configured to perform at least one of: measuring the surface temperature of the affected area at least based on a temperature captured using a thermal imaging camera, or estimating, using an AI-ML model, the surface temperature of the affected area based on visual cues of the affected area present in the plurality of images, the visual cues at least including redness or swelling, wherein the AI-ML model is trained with a plurality of sample injury images and respective temperature data to classify each visual cue with a respective temperature value;

compare, using the AI-ML model, the captured plurality of images with baseline images or a digital twin to detect change in at least one of: size, shape, or contour of the affected area, wherein the AI-ML model is trained, using a plurality of sample injury images, to detect the change in the at least one of: size, shape, or contour of the affected area and to classify signs of swelling in the sample injury images, and wherein the AI-ML model is trained using at least one of Harris Corner Detection, Shi-Tomasi Corner Detection, Canny Edge Detection, Blob Detection, or Scale-Invariant Feature Transform (SIFT);

identify swelling related data indicative of the swelling in the affected area based on the detected change in the at least one of: size, shape, or contour of the affected area;

correlate the swelling related data with the determined surface temperature to assess an underlying issue;

generate a severity index based on the correlation between the swelling related data and the determined surface temperature; and display, via the application interface of the smart phone device, one or more recommendations along with the severity index to the user.

7. The AI based device of claim 6, wherein the one or more recommendations are based on the severity index and at least include seeking medical attention, applying first aid, or monitoring existing condition.

8. The AI based device of claim 6, wherein the at least one processor is configured to:

receive a plurality of sample images of each human body part; and train the AI-ML model with the plurality of sample images of each body part for classifying each body part.

9. The AI based device of claim 6, wherein the at least one processor is configured to:

provide the AI-ML model with the baseline images, wherein the baseline images are captured before injury.

10. The AI based device of claim 6, wherein the at least one processor is configured to:

receive a plurality of images of a person before an injury; and generate, using, an extended reality model, the digital twin of the person beforehand for comparison.

11. A non-transitory computer-readable medium having computer-readable instructions that when executed by a processor causes the processor to perform operations of:

capturing, using an image sensor of a smart phone device, a plurality of images of an affected area from different angles, wherein an application interface of the smart phone device guides a user to align the smart phone device at the different angles;

determining surface temperature of the affected area, wherein the surface temperature indicates potential inflammation or infection, and wherein the determining comprises at least one of: measuring the surface temperature of the affected area at least based on a temperature captured using a thermal imaging camera, or estimating, using an AI-ML model, the surface temperature of the affected area based on visual cues of the affected area present in the plurality of images, the visual cues at least including redness or swelling, wherein the AI-ML model is trained with a plurality of sample injury images and respective temperature data to classify each visual cue with a respective temperature value;

comparing, using the AI-ML model, the captured plurality of images with baseline images or a digital twin to detect change in at least one of: size, shape, or contour of the affected area, wherein the AI-ML model is trained, using a plurality of sample injury images, to detect the change in the at least one of: size, shape, or contour of the affected area and to classify signs of swelling in the sample injury images, and wherein the AI-ML model is trained using at least one of Harris Corner Detection, Shi-Tomasi Corner Detection, Canny Edge Detection, Blob Detection, or Scale-Invariant Feature Transform (SIFT);

identifying swelling related data indicative of the swelling in the affected area based on the detected change in the at least one of: size, shape, or contour of the affected area;

correlating the swelling related data with the determined surface temperature to assess an underlying issue;

generating a severity index based on the correlation between the swelling related data and the determined surface temperature; and displaying, via a user interface of the smart phone device, one or more recommendations along with the severity index to the user.

* * * * *